US012797576B2

(12) United States Patent
Amar et al.

(10) Patent No.: US 12,797,576 B2
(45) Date of Patent: Nov. 17, 2026

(54) URINARY CATHETER SYSTEM AND METHOD FOR SELF-CATHETERIZATION AND URINE EXTRACTION

(71) Applicant: ASIC MEDICAL BUHA LTD, Tel Aviv (IL)

(72) Inventors: Tomer Amar, Tel Aviv (IL); Ariel Michaeli, Karmiel (IL); Avi Ben Shlomo, Tel Aviv (IL); Lior Amar, Tel Aviv (IL); Ilan Yossef Leibovitch, Tel Aviv (IL)

(73) Assignee: ASIC MEDICAL BUHA LTD, Tel Aviv (IL)

( * ) Notice: Subject to any disclaimer, the term of this patent is extended or adjusted under 35 U.S.C. 154(b) by 231 days.

(21) Appl. No.: 18/563,215

(22) PCT Filed: May 23, 2022

(86) PCT No.: PCT/IL2022/050539
§ 371 (c)(1),
(2) Date: Nov. 21, 2023

(87) PCT Pub. No.: WO2022/249169
PCT Pub. Date: Dec. 1, 2022

(65) Prior Publication Data

US 2024/0226501 A1 Jul. 11, 2024

Related U.S. Application Data

(60) Provisional application No. 63/257,071, filed on Oct. 18, 2021, provisional application No. 63/192,630, filed on May 25, 2021.

(51) Int. Cl.
*A61M 25/00* (2006.01)
*A61M 25/01* (2006.01)

(52) U.S. Cl.
CPC .... *A61M 25/0017* (2013.01); *A61M 25/0113* (2013.01); *A61M 2202/0014* (2013.01);
(Continued)

(58) Field of Classification Search
CPC .......... A61M 25/0017; A61M 25/0113; A61M 2202/0014; A61M 2202/0496;
(Continued)

(56) References Cited

U.S. PATENT DOCUMENTS 4,342,313 A * 8/1982 Chittenden ........ A61M 25/0113 604/523
2002/0087131 A1 7/2002 Wolff
(Continued)

FOREIGN PATENT DOCUMENTS

CN 209827184 U 12/2019
EP 0653928 B1 10/2022
(Continued)

OTHER PUBLICATIONS

International Search Report for PCT/IL2022/050539 dated Jul. 31, 2022.

*Primary Examiner* — Rebecca E Eisenberg
*Assistant Examiner* — Katherine-Ph Minh Pham
(74) *Attorney, Agent, or Firm* — The Roy Gross Law Firm, LLC; Roy D. Gross

(57) ABSTRACT

The present invention relates to a catheter system for urine extraction comprising: (a) a genital adapter configured to fit a genitalia; (b) an adapter base connected to said genital adapter; (c) an operational tube connected to said adapter base; (d) a base unit, connected to said operational tube, and comprising an electric pump and a controller; (e) at least one control interface for commanding said controller; (f) a catheter tube having a first end for insertion into said base unit and having a second end for insertion into said opera-
(Continued)

tional tube, said adapter base, and said genital adapter; and (g) wherein said second end of said catheter tube is configured to extend through said genital adapter to the urinal bladder and to extract urine from said urinal bladder by said electric pump.

16 Claims, 4 Drawing Sheets

(52) U.S. Cl.
CPC . *A61M 2202/0496* (2013.01); *A61M 2205/10* (2013.01); *A61M 2205/273* (2013.01); *A61M 2205/3327* (2013.01); *A61M 2205/3331* (2013.01); *A61M 2205/3368* (2013.01); *A61M 2205/502* (2013.01); *A61M 2205/58* (2013.01); *A61M 2210/1085* (2013.01); *A61M 2210/1092* (2013.01); *A61M 2210/1096* (2013.01)

(58) Field of Classification Search
CPC ........ A61M 2205/10; A61M 2205/273; A61M 2205/3327; A61M 2205/3331; A61M 2205/3368; A61M 2205/502; A61M 2205/58; A61M 2210/1085; A61M 2210/1092; A61M 2210/1096; A61M 1/65; A61M 1/87; A61M 2210/1089; A61M 1/73; A61M 39/12; A61F 5/451; A61F 5/453; A61F 5/455
See application file for complete search history.

(56) References Cited

U.S. PATENT DOCUMENTS

| | | | | |
|---|---|---|---|---|
| 2010/0130923 | A1* | 5/2010 | Cleary ............... | A61M 25/0113 606/41 |
| 2018/0264226 | A1* | 9/2018 | Erbey, II ........... | A61M 25/0026 |
| 2019/0143078 | A1* | 5/2019 | Tierney .............. | A61M 25/0113 604/544 |
| 2020/0030575 | A1* | 1/2020 | Bogusky ........... | A61M 16/0488 |
| 2021/0236771 | A1* | 8/2021 | Turner ............... | A61M 25/0113 |

FOREIGN PATENT DOCUMENTS

| | | | |
|---|---|---|---|
| WO | 9403214 | A2 | 2/1994 |
| WO | 2017015351 | A1 | 1/2017 |

* cited by examiner

URINARY CATHETER SYSTEM AND METHOD FOR SELF-CATHETERIZATION AND URINE EXTRACTION

TECHNICAL FIELD

The present invention relates to catheter systems. More particularly, to self-catheterization and urine extraction systems.

BACKGROUND

Some existing non-surgical solutions for people who suffer from urinary retention may include insertion of a urethral catheter for draining the bladder. Such catheter may be inserted permanently or occasionally, for example every few hours, e.g. by Clean Intermittent Catheterisation (CIC).

A typical permanent catheter is thick and cumbersome and usually causes inconvenience to patients. The CIC catheter is usually slenderer, in order to enable self-insertion of the catheter by the patients. However, it is still painful and intimidating for the patients to perform the insertions. In many cases, due the pain and fear of the patients, and in order to refrain from harm to the kidneys, a permanent insertion or other medical or surgical interventions are performed.

An exemplary catheterization system described in the paper "Efficacy and safety of the novel automatic urinary catheterization device" by Kang et al. (https://www.ncbi.nlm.nih.gov/pmc/articles/PMC6319984/), is an automatic urinary catheterization device to induce self-IC for patients with bladder dysfunction and upper extremity disability. However, the described device is too large for comfortable use.

Another exemplary catheterization system described in KR20190080214(A), is a device for automatically inserting a portable catheter that reduces frictional force generated when a catheter is inserted into urethra as lubricating liquid stored in a tank is discharged to an adsorption sponge covering a pipe transfer passage when a disposable guide capable of holding a penis is coupled to a main body. The device comprises: a main body having an outer shape gripped by a user; a disposable guide having a mounting groove having a shape to which a penis of a human being can be held, having a pipe transfer passage penetrating forward and backward from a position corresponding to urethra of the penis held in the mounting groove, and coupled to the main body to be detached; a catheter transfer unit for transferring a catheter forward, which is inserted into the pipe transfer passage; and a lubricating liquid application unit capable of applying a lubricating liquid onto the catheter transferred through the pipe transfer passage. However, the described system is too large for comfortable use.

It would therefore be desired to propose a system void of these deficiencies.

SUMMARY

It is an object of the present invention to provide a comfortable self-catheterization and urine extraction system.

It is another object of the present invention to provide a portable catheter system that can be used at home.

It is still another object of the present invention to provide an all-gender catheter system for easy self-insertion.

Other objects and advantages of the invention will become apparent as the description proceeds.

The present invention relates to a catheter system for urine extraction comprising: (a) a genital adapter configured to fit a genitalia; (b) an adapter base connected to said genital adapter; (c) an operational tube connected to said adapter base; (d) a base unit, connected to said operational tube, and comprising an electric pump and a controller; (e) at least one control interface for commanding said controller; (f) a catheter tube having a first end for insertion into said base unit and having a second end for insertion into said operational tube, said adapter base, and said genital adapter; and (g) wherein said second end of said catheter tube is configured to extend through said genital adapter to the urinal bladder and to extract urine from said urinal bladder by said electric pump.

Preferably, the system further comprises a detachable container.

Preferably, the system further comprises at least one of the following sensors: a temperature sensor, a humidity sensor, a mechanical resistance sensor, an electrical resistance sensor, or a pressure sensor.

Preferably, the sensor monitors at least one of the following conditions around the catheter tube: electrical resistance, mechanical resistance, temperature, pressure or humidity.

Preferably, the genital adapter and/or the catheter tube, and/or the adapter base are disposable single-use items.

In one embodiment, the system further comprises controls for the insertion and retraction of catheter tube into or out from the urethra.

In one embodiment, the system automatically controls the insertion and retraction of catheter tube into or out from the urethra.

In one embodiment, the system further comprises controls for the extraction of the urine out from the bladder.

In one embodiment, the system automatically controls the extraction of the urine out from the bladder.

In one embodiment, the genital adapter is a male genital adapter.

In one embodiment, the genital adapter is a female genital adapter.

In one embodiment, the system further comprises an actuator for pushing the second end of the catheter tube through the genital adapter and forward into the urethra.

In one embodiment, the catheter is held in a capsule.

In one embodiment, the system further comprises a motor for pushing the second end of the catheter tube, in the capsule, through the genital adapter and forward into the urethra.

The present invention also relates to a method for urine extraction comprising: (a) providing a genital adapter configured to fit a genitalia; (b) providing an adapter base connected to said genital adapter; (c) providing an operational tube connected to said adapter base; (d) providing a base unit, connected to said operational tube, and comprising a pump; (e) providing a catheter tube; (f) inserting a first end of said catheter tube into said base unit; (g) inserting a second end of said catheter tube into said genital adapter; (h) extending said second end of said catheter tube through said genital adapter to the urinal bladder; and (i) extracting urine from said urinal bladder, using said catheter, by said pump.

BRIEF DESCRIPTION OF THE DRAWINGS

The accompanying drawings, and specific references to their details, are herein used, by way of example only, to illustratively describe some of the embodiments of the invention.

Identical or duplicate or equivalent or similar structures, elements, or parts that appear in one or more drawings are generally labeled with the same reference numeral, optionally with an additional letter or letters to distinguish between similar entities or variants of entities and may not be repeatedly labeled and/or described. References to previously presented elements are implied without necessarily further citing the drawing or description in which they appear.

BRIEF DESCRIPTION OF THE DRAWINGS

Figure 1A:
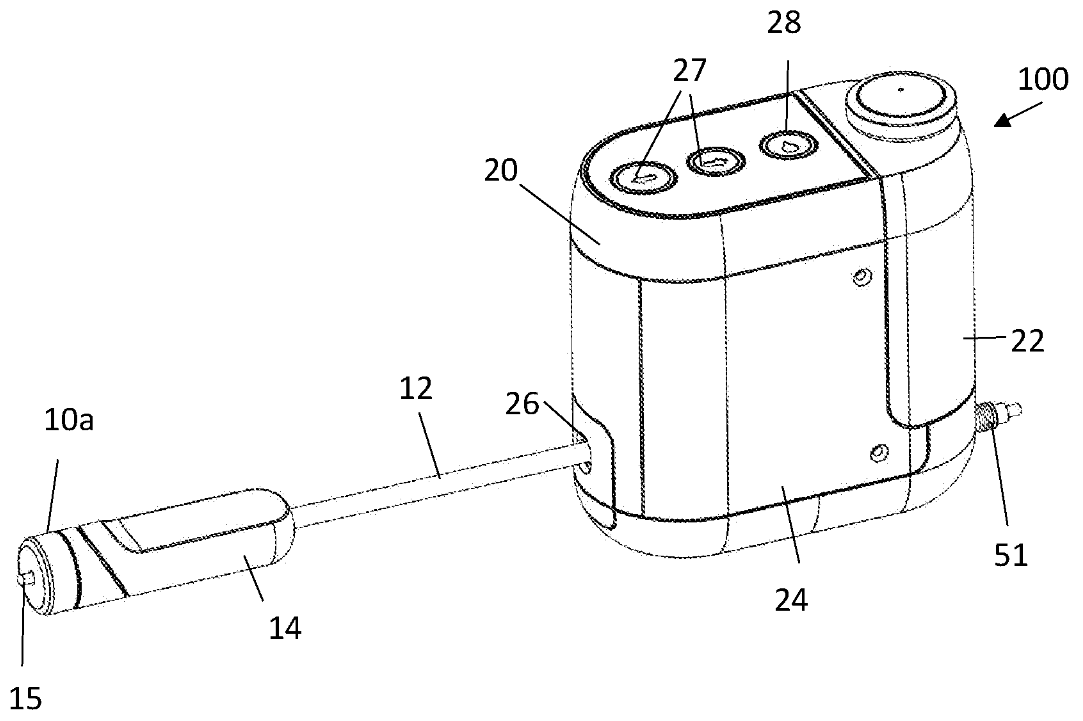

FIG. 1A is a diagram of a system for self-catheterization and urine extraction, and a genital connector configured for catheterization, according to an embodiment of the invention.

Figure 1B:
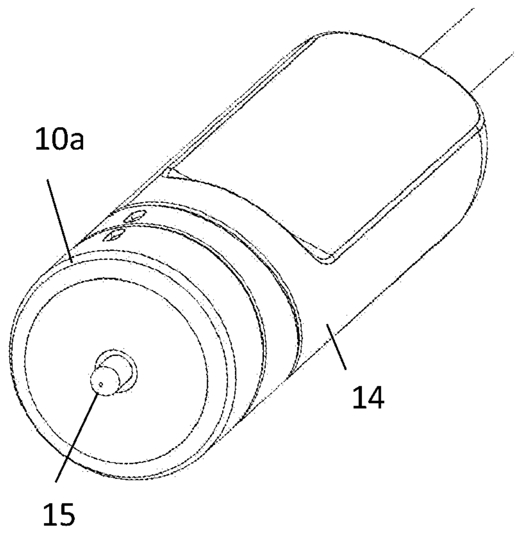

FIG. 1B is a diagram of a male genital adapter and the adapter base from another angle, according to an embodiment.

Figure 1C:
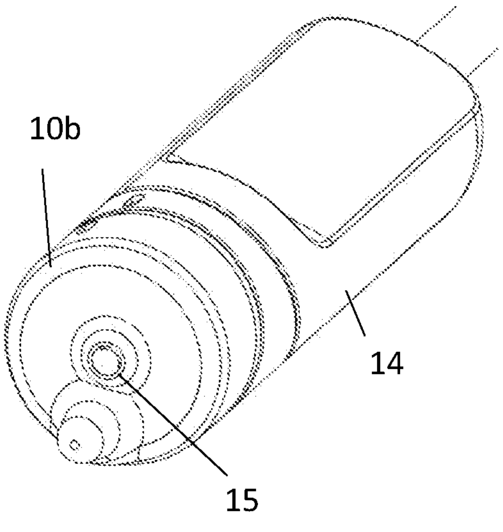

FIG. 1C is a diagram of a female genital adapter and the adapter base, according to an embodiment.

Figure 2:
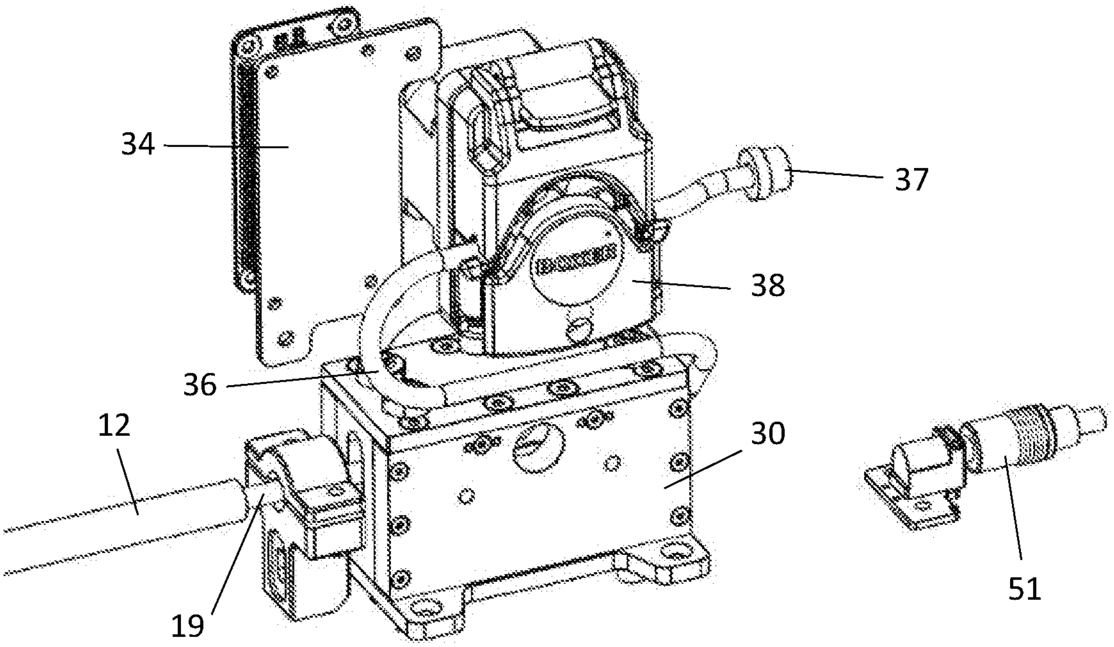

FIG. 2 is a diagram of the system for self-catheterization and urine extraction, where the outer part of base unit is removed, for showing some of the internal components of the system, according to an embodiment.

Figure 3:
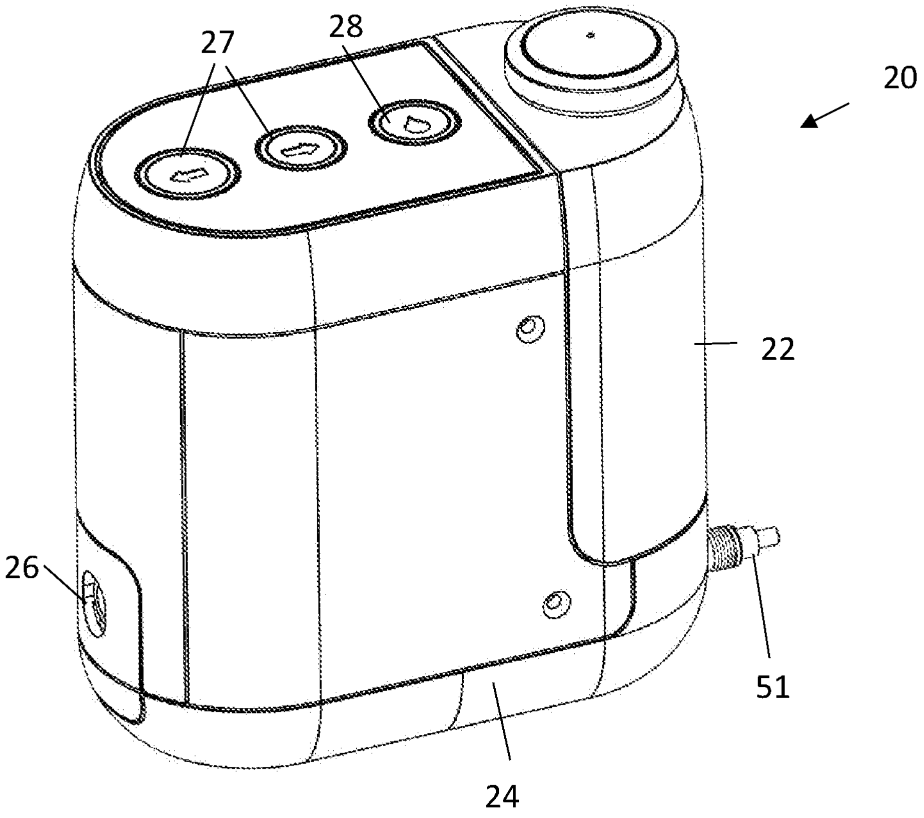

FIG. 3 is a diagram of the base unit of the system for self-catheterization and urine extraction, according to an embodiment.

Figure 4:
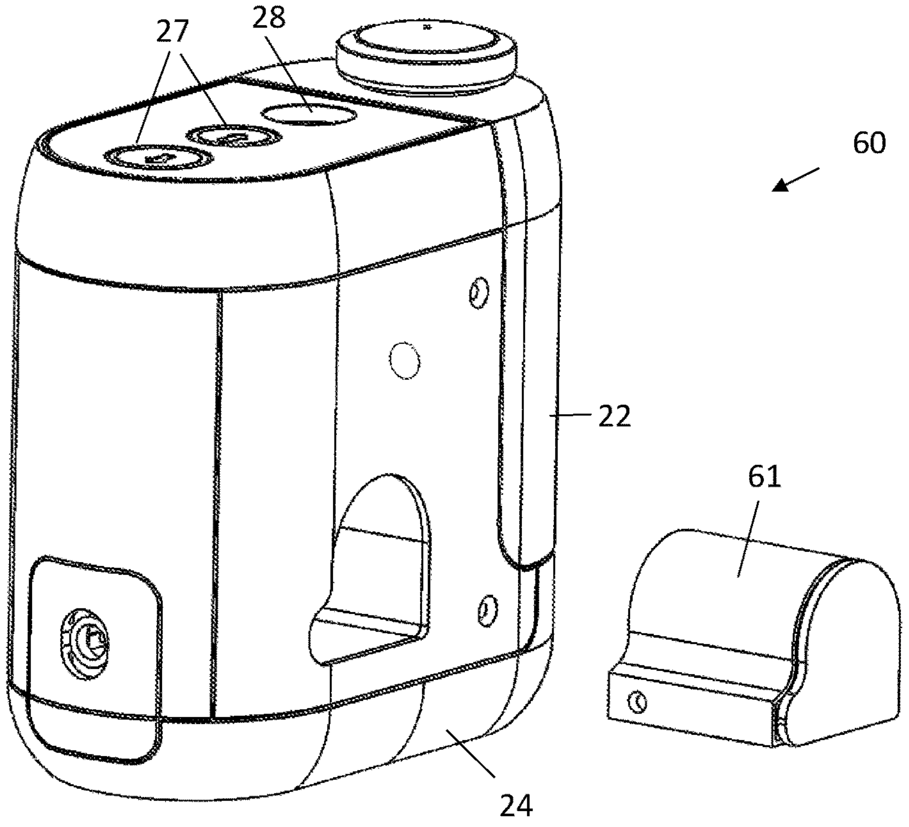

FIG. 4 is a diagram of the base unit of the system for self-catheterization and urine extraction, according to another embodiment.

Figure 5:
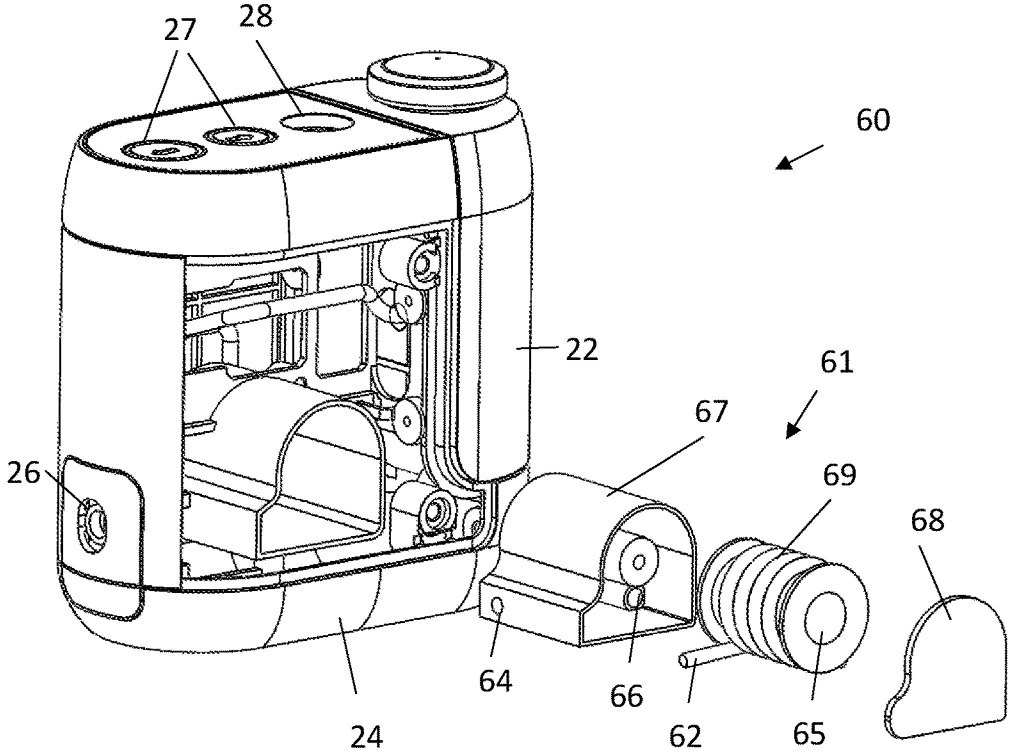

FIG. 5 is a diagram, from the front, of the base unit of the system for self-catheterization and urine extraction, where the front-panel is removed from the base unit, for showing some of the internal components of the system according to an embodiment.

Figure 6:
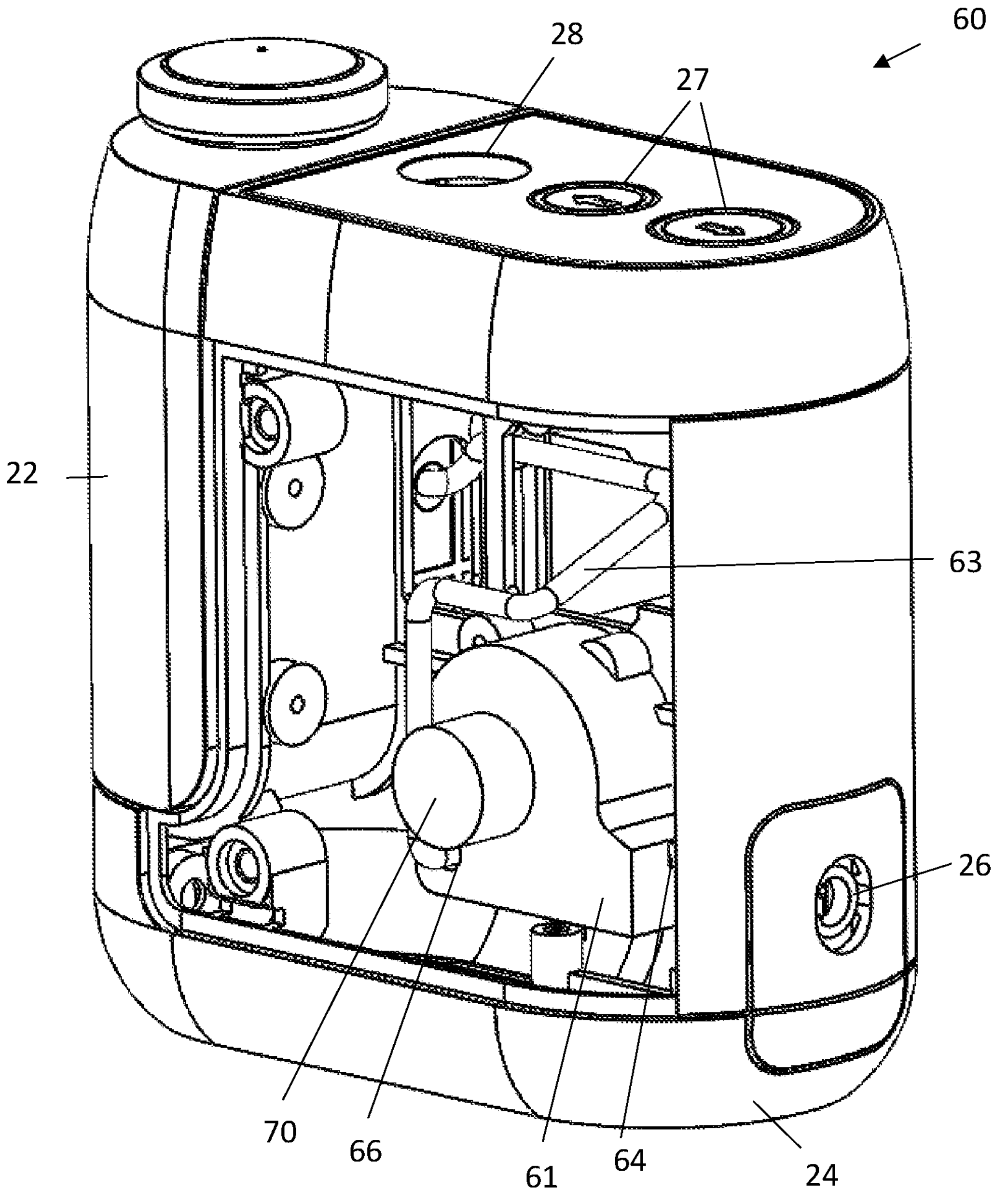

FIG. 6 is a diagram, from the rear, of the base unit of the system for self-catheterization and urine extraction, where the rear-panel is removed from the base unit, for showing some of the internal components of the system according to an embodiment.

DETAILED DESCRIPTION

The terms of “front”, “rear”, “down”, “up”, “bottom”, “upper”, “horizontal”, “vertical”, “right”, “left” or any reference to sides or directions are used throughout the description for the sake of brevity alone and are relative terms only and not intended to require a particular component orientation.

The system, according to some embodiments of the present disclosure, enables a controlled and efficient extraction of urine, by using an electrical pump. This enables the use of a significantly narrower catheter tube, which reduces the inconvenience caused to the user by the insertion. For example, a catheter tube according to some embodiments of the present invention may have an external diameter of about 2 to 5 millimeters. In one embodiment, the catheter tube may have an external diameter between 2-3 mm. In one embodiment, the catheter tube may have an external diameter between 3-4 mm. In one embodiment, the catheter tube may have an external diameter between 4-5 mm. In one embodiment, the catheter tube may have an external diameter between 3.18-3.82 mm. In one embodiment, the catheter tube may have an external diameter corresponding to 10 FR of the French scale known in the art. In one embodiment, the catheter tube may have an external diameter corresponding to 12 FR of the French scale known in the art.

Some embodiments of the present disclosure provide a system and method for automatic urinary self-catheterization and extraction, which facilitates a much easier and pleasant self-catheterization than the current typical methods. In some embodiments, the disclosed system is intended for home use, and does not require a medical professional for its day-to-day operation, where the user can self-insert the catheter and can self-extract his own urine using the system described below, such as described below in relations to FIG. 1A.

In some embodiments of the present disclosure, the user may control in a continuous manner the catheter insertion.

FIG. 1A is a diagram of a system 100 for self-catheterization and urine extraction, and a genital connector configured for catheterization, according to an embodiment of the invention. System 100 comprises a genital adapter, such as genital adapter 10*a*, an operational tube 12, an operational unit 24, comprising an electric pump and a controller, at least one control interface, and other components, as described in more detail below. The genital adapter 10*a* may be connected on an adapter base 14 which may be connected to the operational tube 12. In one embodiment the base unit 20 may also include a container 22, in addition to the operational unit 24, where the container 22 may be configured to receive and contain the urine extracted by system 100. In some embodiments, the control interface may be catheterization controls 27 and/or urine extraction control 28 and/or an application on a mobile device, human gestures, or any other known control interface. Operational unit 24 may comprise, for example, a hatch 26, catheterization controls 27, a urine extraction control 28, and/or various components that control, actuate and/or operate system 100, for example as described in more detail below in relations to FIG. 2. In one embodiment the system 100 may have an electrical socket 51 for supplying power to the system.

In an exemplified operation, a first end (not shown) of a catheter tube may be inserted into the genital adapter 10*a*, into adapter base 14 and into the operational tube 12, as depicted in FIG. 1A, and further advanced into operational unit 24. The second end 15 of the catheter tube may be held by low friction at the adapter base 14. Genital adapter 10*a* may be configured to position the second end 15 of the catheter tube against the opening of the urethra, when adapter 10*a* is correctly placed onto the genitalia. In some embodiments, when the genital adapter 10*a* is positioned against opening of the urethra, the user can press the catheterization controls 27 for extending the second end 15, of the catheter tube, from the genital adapter 10*a* into the urethra. In one embodiment, the user can use the catheterization controls 27 to extend, or retract when needed, the second end 15 of catheter tube until it reaches the urinary bladder. Once the second end 15 of catheter tube reaches the urinal bladder, the user can then use the urine extraction control 28 to operate the system and pump the urine from the urinary bladder. After the urine has been extracted, from the urinary bladder, the user can retract the second end 15 of catheter tube from the urinary bladder, and the urethra, back into the genital adapter 10*a*. In some embodiments, FIG. 1B is a diagram of the genital adapter 10*a* and the adapter base 14 from another angle, according to an embodiment. The genital adapter 10*a* may be a male genital adapter and it may be configured, for example, for catheterization of male genitalia. In some embodiments, the genital adapter 10*a* may be connected to the adapter base 14, by a screw, snap-in-place, rotating, or any known connecting means. In other embodiments the genital adapter 10*a* may be a permanent part of the adapter base 14.

FIG. 1C is a diagram of a female genital adapter 10*b* and the adapter base 14, according to an embodiment. Genital adapter 10*b* may be configured, for example, for the catheterization of a female genitalia. In some embodiments, the alternative genital adapter 10*b* may be utilized, as shown for example in FIG. 1C, for replacing the adapter 10*a* depicted in FIG. 1B, for catheterization of female genitalia. In some embodiments, a genital adapter 10*b* may be connected to the adapter base 14, by a screw, snap-in-place, rotating, or any known connecting means. In other embodiments, the genital adapter 10*b* may be a permanent part of the adapter base 14.

The genital adapter 10*a* or 10*b* and/or the catheter tube, and/or the adapter base 14 may be a disposable single-use items, for example to ensure sterility of the parts of these items intended to contact and/or penetrate genitalia.

FIG. 2 is a diagram of the system for self-catheterization and urine extraction, where the outer part of base unit 20 is removed, for showing some of the internal components of the system, according to an embodiment. The operational unit, of the system, as described in relation to FIG. 1A, may comprise an actuator 30, a controller 34, a guiding tube 36 and a pump 38. Guiding tube 36 may connect between actuator 30 and pump 38. According to some embodiments, when catheter tube 19 is inserted through the operational tube 12, it is further inserted into actuator 30 and into guiding tube 36. In some embodiments, a seal (not shown) may be positioned between the guiding tube 36 and the actuator 30. In some embodiments, an elastic seal (not shown) may be positioned between the guiding tube 36 and catheter tube 19. In some embodiments, the first end of catheter tube 19 goes further into tube 36, for example until the entire length of tube 19 is inside the base unit. In some embodiments the operational unit, of the system, may receive its power by electrical input 51.

In operation, a first end of catheter tube 19 may be inserted into the operational tube 12, as described in relations to FIG. 2, and the catheter tube 19 may be further advanced into operational unit 24. A second end of catheter tube 19 may be held by low friction at a base 14 which has a genital adapter 10*a* or 10*b*, attached as described in relations to FIG. 1B-1C. Genital adapter 10*a* or 10*b* may be configured to position the second end of catheter tube 19 against opening of the urethra, when adapter 10*a* or 10*b* is correctly placed on the genitalia. By operational unit 24, the catheter tube 19 may be inserted into the urethra, and urine may be extracted out from the bladder, for example into container 22. When urine extraction is complete, catheter tube 19 may be retracted and removed from the urethra.

In some embodiments, guiding tube 36 may extend into the container 22, as described in relations to FIGS. 1-2, guiding the extracted urine into container 22. At the end of guiding tube 36 that extends into container 22, guiding tube 36 may include a seal or valve 37, configured to prevent urine from returning from container 22 into tube 36.

FIG. 3 is a diagram of the base unit 20 of the system for self-catheterization and urine extraction, according to an embodiment. The user may control the initiation and/or halting of the insertion and/or retraction of catheter tube 19, as depicted in relation to FIG. 1, into and/or out from the urethra, for example by controls 27. In some embodiments of the present invention, a user may control the insertion and/or retraction and/or speed of the insertion and/or retraction of catheter tube 19 into and/or out from the urethra, for example by controls 27. In some embodiments of the present invention, for example when the catheter tube 19 is sufficiently inserted into the urethra, a user may control the extraction, e.g. pumping, of the urine out from the bladder, for example by controls 28. Thus, the user may activate the pump by engaging controls 28, for example pushing a button or a switch. The pump may operate as long as the user activates it with controls 28, or until the user deactivates it with controls 28. In some embodiments, as described in more detail herein, system has safety measures for stopping the extraction on thresholds of metrics such as, for example, low pressure.

In some embodiments, a user may control the initiation and/or halting of the extraction, e.g. pumping, of the urine out from the bladder, for example by controls. As described in more detail herein, according to some embodiments, once a user is initiating the insertion and/or retraction of catheter tube into and/or out from the urethra, the operational unit may automatically control the sufficient and safe insertion and/or retraction of the catheter tube. According to some embodiments, once a user is initiating the extraction of urine from the bladder, the operational unit may automatically control the extraction of the urine.

The extracted urine may be received by and contained in container 22, as described in relations to FIG. 1, container 22 may be detached from operational unit 24. The urine may be disposed of at patient's convenience, by detaching container 22 from operational unit 24 and emptying the container 22. Container 22 may be re-attached to operational unit 24, for example after it is emptied and/or cleaned.

In some embodiments, the catheter tube 19, as described in relations to FIG. 2, may be provided inside a protective package (not shown) that maintains its sterility. In some embodiments, catheter tube 19 is inserted into adapter base 14 of adapter 10*a* or 10*b* while still in the protective package. In some embodiments, catheter tube 19 and adapter 10*a* or 10*b* are provided when catheter tube 19 is already inserted into an opening in base 14. In one embodiment, the catheter tube 19 and/or adapter base 14 and/or adapter 10*a* or 10*b* are packaged together in the same protective package In some embodiments, the system may utilize at least one sensor that monitors conditions around the catheter tube, such as, for example electrical resistance, mechanical resistance, temperature, humidity, etc. In some embodiments, sensor(s) may be used for monitoring and identifying thresholds. For example, the sensors may be used to avoid injury when the catheter tube encounters an obstacle and/or a narrow path or to prevent the catheter tube from penetrating the bladder. In some embodiments, sensors may be used for monitoring physical conditions and identifying thresholds. For example, the sensors may be used for checking that the tube is sufficiently inserted in the urethra, and/or for changing the velocity of insertion and/or retraction of the tube, and/or for sufficient extraction of urine, and/or any other suitable thresholds that may be used for controlling the operation of system.

In some embodiments, the system may include a portable power source such as, a battery. For example, the power source may suffice for a certain number of urine cycles, for example about ten cycles in average, and then may be recharged, for example by a supplied compatible charger.

According to some embodiments of the present invention, a first end of catheter tube 19, for example while catheter tube 19 is still sealed in a protective package, may be inserted through the adapter base 14 and further into an actuator 30, as described in relations to FIG. 2. Adapter 10*a* or 10*b* may then be connected, for example screwed, onto base 14. Adapter 10*a* or 10*b* may also be sealed in a protective package. A second end of catheter tube 19 may be held by low friction in an opening at base 14 of adapter 10*a* or 10*b*.

A user may mount a compatible adapter 10*a* or 10*b* onto the genitalia. For example, the user may remove the protective package from adapter 10*a* or 10*b* before placing it onto the genitalia, as described in relations to FIGS. 1-3. When mounted, the adapter positions the second end 15 of the catheter tube 19 at the opening of the urethra. Then, according to some embodiments, the user may initiate insertion of the catheter tube 19 into the urethra, for example by controls 27. When receiving the command by controls 27, actuator 30 may push catheter tube 19 so that the second end of tube 19 pushes through the opening at the base 14 forward into the urethra. According to some embodiments, the user controls the movement of catheter tube 19 inside the urethra, forward and/or backward, for example by pushing buttons and/or switches. For example, the catheter tube 19 is immobile unless the user controls it to move in either direction. For example, once initiating the insertion, actuator 30 may push catheter tube 19 so that the second end of tube 19 pushes through the opening at the base 14 forward into the urethra. In some embodiments, the forward movement causes a tip of tube 19 to break through the protective package of tube 19, for example, so that the tube makes a hole in the package and emerges from the package forward. In some embodiments, a user may use controls 27 to stop the advancement of tube 19 inside the urethra, and/or to retract tube 19 from the urethra.

According to some embodiments of the present disclosure, actuator 30 may be controlled by a controller 34, as described in relations to FIG. 2. Actuator 30 may be configured to advance catheter tube 19 automatically in the urethra, for example until the controller detects the bladder and/or a counter force that resists the advancement of tube 19, for example based on signals received from the sensors. The user may further adjust the position of tube 19 inside the urethra, for example by controls 27.

Actuator 30, as described in relations to FIGS. 1-3 may drive catheter tube 19 by friction on the protection package of tube 19, pressed onto tube 19. The friction between the package and the external walls of tube 19 may be sufficiently high, so that actuator 30 may be able to drive tube 19 together with the package. The protection package may be breached by an end of tube 19, for example, only at an opening at base 14 of the adapter 10*a* or 10*b*, configured to be positioned against the opening of the urethra, when the adapter 10*a* or 10*b* is placed properly onto the genitalia. Other parts of the catheter may remain protected by the package and/or untouched throughout operation.

The extraction of urine from the bladder may be initiated by the user. In some embodiments, the pump may extract the urine until the controller detects that the urine extraction is complete based on sensor signals, for example pressure and/or humidity sensors. For example, when the pressure and/or humidity sensed by the sensors decreases to a certain level, the controller may halt the pump operation. In some embodiments, the urine extraction and/or the pump operation may be halted and/or initiated by the controls.

In some embodiments, a user may initiate the removal, e.g. retraction, of the catheter tube 19, as described in relation to FIGS. 1-3 from the urethra. In some embodiments, the removal, e.g. retraction, of the catheter tube 19 is initiated when the pump operation is halted and/or the urine extraction is completed. In some embodiments, base unit 20 may include a visual or vocal indicator, such as a led indicator, that may indicate when the urine extraction is complete. The controller may retract the catheter tube 19 out from the urethra by actuator 30. The user may remove adapter 10*a* or 10*b* and/or catheter tube 19 from the genitalia and/or from base unit 20 and dispose of adapter 10*a* or 10*b* and/or tube 19 and/or adapter base 14.

In some embodiments, the system may include visual and/or vocal indicators.

According to some embodiments, when catheter tube 19 is inserted through the operational tube 12, as described in relations to FIGS. 1-3, it is further inserted into actuator 30 and into guiding tube 36. A seal may be positioned where guiding tube 36 is connected to actuator 30. After the full insertion of tube 19 into base unit 20, and/or when extraction of urine from the bladder starts, the protective package of tube 19 may be breached at the first end of tube 19, allowing urine to be pumped out of catheter tube 19 by pump 38. In some embodiment, the negative pressure provided by pump 38, tears the protective package at the edge at the first and/or second end of tube 19. In other embodiment, another mechanism, such as, for example, a pin inside tube 36 and/or unit 20, may breach the protective package at the first end of tube 19, for example once tube 19 is fully inserted into base unit 20, and/or when or just before extraction of urine from the bladder begins.

In one embodiment, actuator 30, as described in relations to FIG. 2, drives catheter tube 19, for example by a servo mechanism, for example including a servo gear and/or a counter bearing. The protective package of catheter tube 19 may have high friction with tube 19, such that actuator 30 may drive catheter tube 19 together with its package. For example, the protective package may be internally coarse, such as to create static friction with catheter tube 19. The mechanism of actuator 30 may tighten around tube 19 with its package and drive both package and tube 19 to the desired direction. The protective package may also be externally coarse, providing friction between the package and actuator 30. In some embodiments of the present disclosure, package slack may be accumulated, for example when tube 19 is driven into the urethra, near the opening at base 14. This slack may be collected into a designated clearing (not shown) in the system.

In some embodiments, actuator 30 may include a sensor that measures an indication of mechanical resistance in driving tube 19, that may indicate resistance of the urethra and/or the bladder opening, and/or may be used by controller 34 as a trigger for auto-stopping the advancement of tube 19 inside the urethra. For example, the sensor (not shown) may measure current as indication of mechanical pressure.

FIG. 4 is a diagram of the base unit 60 of the system for self-catheterization and urine extraction, according to another embodiment. In this embodiment a capsule 61 comprising the catheter tube maybe inserted into the base unit 60. In one embodiment the capsule 61, comprising the catheter tube, is a disposable capsule. After the user has inserted the capsule 61 into the base unit 60, he may control the initiation and/or halting of the insertion or retraction of the catheter tube, into or out from the operational tube 12, into or out from adapter base 14, into or out from the genital adapter, and into or out from the urethra, for example by controls 27. In some embodiments of the present invention, a user may control the insertion or retraction and/or speed of the insertion or retraction of catheter tube into or out from the urethra using a control interface, for example by controls 27. In some embodiments of the present invention, for example when the catheter tube is sufficiently inserted into the urethra, a user may control the extraction, e.g. pumping, of the urine out from the bladder using a control interface, for example by controls 28. Thus, the user may activate the pump by engaging controls 28, for example pushing a button or a switch. The pump may operate as long as the user activates it with controls 28, or until the user deactivates it with controls 28. In some embodiments, as described in more detail above, the system has safety measures for stopping the extraction on thresholds of metrics such as, for example, low pressure. In some embodiments, the system automatically controls the extraction of the urine out from the bladder.

FIG. 5 is a diagram, from the front, of the base unit 60 of the system for self-catheterization and urine extraction, where the front-panel is removed from the base unit 60, for showing some of the internal components of the system according to an embodiment. In this diagram the pump is not depicted, for the sake of brevity. In this diagram the capsule 61 is depicted in a blown-out diagram for showing some of the internal components of the capsule 61. In one embodiment, the capsule 61 comprises the catheter tube 69, which is rolled on a drum 65, a cover 67, and the cap 68 for closing the capsule 61. The closed capsule 61, as described in relations to FIG. 4, can be inserted into the base unit 60, where an inner motor (not shown) can turn the drum 65 and unroll catheter tube 69. The motor can unroll the second end 62 of the catheter tube 69 through the hole 64 and through the hatch 26 towards the operational tube 12 and base 14, as described in relations to FIG. 1. In this embodiment, the motor of the capsule substitutes the actuator, described in relations to FIG. 2, where the motor may push catheter tube 69 so that the second end of tube 69 pushes through the opening at the base 14, and the genital adapter, forward into the urethra. The first end of the catheter tube 69 may be attached and sealed to the pipe 66 of the cover 67.

FIG. 6 is a diagram, from the rear, of the base unit 60 of the system for self-catheterization and urine extraction, where the rear-panel is removed from the base unit 60, for showing some of the internal components of the system according to an embodiment. In this diagram the pump is not depicted as well, for the sake of brevity. In some embodiments, the guiding tube 63 is positioned to connect and seal, at one end, to the pipe 66, of the capsule 61, which is attached and sealed to the first end of the catheter tube, as described in relations to FIG. 5. The other end of pipe 63 may extend into the container 22, as described in relations to FIGS. 1-2. Guiding tube 63 may connect between capsule 61, the pump, and the container 22. In some embodiments, a seal (not shown) may be positioned between the guiding tube 63 and the capsule 61. In some embodiment the motor 70 can unroll the catheter tube within the capsule 61. The motor 70 can unroll the second end of the catheter tube through the hole 64 and through the hatch 26 towards the operational tube 12 and base 14 and into the urethra, as described in relations to FIG. 1.

Once the second end of catheter tube 69 reaches the urinal bladder the urine can be pumped from the urinary bladder, by the user or automatically, as described in relations to FIG. 4-6. After the urine has been extracted, from the urinary bladder, the second end of catheter tube 69 can be retracted from the urinary bladder by motor 70 that can re-roll the catheter tube on the drum 65 back into the capsule 61. Once the catheter tube 69 has been rolled, onto the drum 65 and into the capsule 61, the capsule 61 can be released from the base unit 60 of the system and replaced by a new capsule. In one embodiment, the insertion and retraction of catheter tube 69 into or out from the urethra, by the motor 70, may be controlled by the user, using a control interface such as controls 27. In another embodiment, the insertion and retraction of catheter tube 69 into or out from the urethra, by the motor 70, may be automatically controlled by the system, such as by the controller of the system.

In some embodiments the catheter tube 69, as described in relations to FIGS. 5-6, may be provided inside a protective package (not shown) that maintains its sterility inside the capsule 61. In an embodiment, the protective package may be breached by an end of tube 69, driven by motor 70, for example, only at the opening of the adapter 10*a* or 10*b*.

According to some embodiments of the present disclosure, the system may include a temperature sensor, a humidity sensor, a mechanical resistance sensor, an electrical resistance sensor, a battery status sensor and/or a pressure sensor. In some embodiments, the sensor circuits will be housed in the base unit. In some embodiments, the sensor(s) may be located on the catheter tube and may be electrically connected by the actuator or by the capsule to the controller. In some embodiments, humidity and/or temperature sensor data may be analyzed for anomalies, for example by the controller, for performing as robust reliable trigger indicators of reaching the bladder by the second end of tube. In some embodiments, mechanical resistance and/or pressure sensors may be analyzed for pre-configured thresholds. For example, resistance may be a trigger to stop motion of the catheter tube. Pressure may be a trigger to stop operation of the pump. Nominal threshold values may be, for example, 30 grams equivalent in resistance and/or 1 atm in pressure, respectively.

Controller 34 may receive data from sensors and/or user commands through the control interface, such as controls 27 and/or 28, as described in relations to FIGS. 1-6. Controller 34 may control pump 38, actuator 30 or motor 70, and/or visual/vocal indicators. Controller 34 may control the various components of system 100 according to user commands and automatic responses to sensor data. Controller 34 may indicate to the user various conditions, such as, for example, when tube reached the bladder and/or when the urine extraction is finished.

Pump 38 may be a peristaltic pump and may be used to extract urine from the bladder into container 22, as described in relations to FIGS. 1-6. In some embodiments, the mechanism and/or structure of pump 38 is configured for sealing the urine inside the guiding tube, without allowing contact of the urine with other parts of the pump. For example, in some embodiments, pump 38 is configured to pump flow of 400-600 ml/min. A seal may ensure vacuum is created by pump 38 in guiding tube 36.

In some embodiments, before use of the catheter and after installing the adaptor 10*a* or 10*b*, described in relations to FIGS. 1B-C, the user can rotate the adapter 10*a* or 10*b* for driving an inner blade inside the adapter 10*a* or 10*b* to breach the sealed cover of the catheter 19 or 69. In some embodiments, safety measures can be taken to ensure the breaching of sealed cover prior to use.

In some embodiments, the system may be used to pump water or disinfection material through some of the components of the system for cleaning these components after use.

While the above description discloses many embodiments and specifications of the invention, these were described by way of illustration and should not be construed as limitations on the scope of the invention. The described invention may be carried into practice with many modifications which are within the scope of the appended claims.

The invention claimed is:

1. A catheter system for urine extraction comprising:

a genital adapter configured to fit a genitalia;

an adapter base connected to said genital adapter;

an operational tube connected to said adapter base;

a base unit, connected to said operational tube, and comprising an electric pump and a controller;

at least one control interface for commanding said controller;

a catheter tube having a first end for insertion into said base unit and having a second end for insertion into said operational tube, said adapter base, and said genital adapter;

a disposable capsule insertable into said base unit, said disposable capsule is comprised of a drum on which said catheter tube is rolled, either an actuator or a motor for pushing the second end of the catheter tube through the genital adapter and forward into the urethra;

wherein said second end of said catheter tube is configured to extend through said genital adapter to the urinal bladder and to extract urine from said urinal bladder by said electric pump, wherein in case said motor is used, said motor is pushing the second end of the catheter tube, in said disposable capsule, through the genital adapter and forward into the urethra, said motor turning the drum and thus unrolling and pushing the catheter tube so that the second end of the catheter tube pushes through an opening in the base unit, and pushes through the genital adapter, forward into the urethra.

2. The system according to claim 1, wherein the system further comprises a detachable container.

3. The system according to claim 1, wherein the system further comprises at least one of the following sensors: a temperature sensor, a humidity sensor, a mechanical resistance sensor, an electrical resistance sensor, or a pressure sensor.

4. The system according to claim 3, wherein the sensor monitors at least one of the following conditions around the catheter tube: electrical resistance, mechanical resistance, temperature, pressure, or humidity.

5. The system according to claim 1, wherein the genital adapter and/or the catheter tube, and/or the adapter base are disposable single-use items.

6. The system according to claim 1, wherein the system further comprises controls for the insertion and retraction of catheter tube into or out from the urethra.

7. The system according to claim 1, wherein the system automatically controls the insertion and retraction of catheter tube into or out from the urethra.

8. The system according to claim 1, wherein the system further comprises controls for the extraction of the urine out from the bladder.

9. The system according to claim 1, wherein the system automatically controls the extraction of the urine out from the bladder.

10. The system according to claim 1, wherein the genital adapter is a male genital adapter.

11. The system according to claim 1, wherein the genital adapter is a female genital adapter.

12. The system according to claim 1, wherein after the urine has been extracted from the urinary bladder, the second end of the catheter tube is retracted from the urinary bladder and re-rolled on the drum in said insertable capsule by said motor.

13. The system according to claim 12, wherein once the catheter tube has been rolled, onto the drum and into the disposable capsule, the disposable capsule can be released from the base unit of the system and replaced by a new capsule.

14. The system according to claim 1, wherein the first end of the catheter tube is connected to a pipe extended to a container to draw urine thereto.

15. The system according to claim 1, wherein once the second end of catheter tube reaches the urinal bladder, urine is pumpable from the urinary bladder either automatically via the controller of the system or by a user via a control interface.

16. A method for urine extraction comprising:

providing a genital adapter configured to fit a genitalia;

providing an adapter base connected to said genital adapter;

providing an operational tube connected to said adapter base;

providing a base unit comprised of a disposable insertable capsule comprised of a drum on which a catheter tube is rolled, either an actuator or a motor, and a pump;

inserting a first end of said catheter tube into said disposable insertable capsule;

inserting a second end of said catheter tube into said genital adapter;

extending and pushing said second end of said catheter tube through said genital adapter to the urinal bladder; and extracting urine from said urinal bladder, using said catheter, by said pump.

* * * * *